(12) United States Patent
Grunhut et al.

(10) Patent No.: US 8,568,358 B2
(45) Date of Patent: Oct. 29, 2013

(54) DEVICE FOR AUTOMATIC DELIVERY OF SUCCESSIVE DOSES OF PRODUCT

(75) Inventors: Guillaume Grunhut, Grenoble (FR); Patrick Dupuis, Jarrie (FR)

(73) Assignee: Becton Dickinson France, Le Pont de Claix (FR)

( * ) Notice: Subject to any disclaimer, the term of this patent is extended or adjusted under 35 U.S.C. 154(b) by 899 days.

(21) Appl. No.: 12/514,625

(22) PCT Filed: Nov. 15, 2007

(86) PCT No.: PCT/IB2007/004324
§ 371 (c)(1),
(2), (4) Date: Jan. 11, 2010

(87) PCT Pub. No.: WO2008/059385
PCT Pub. Date: May 22, 2008

(65) Prior Publication Data
US 2010/0145275 A1    Jun. 10, 2010

(51) Int. Cl.
*A61M 5/20* (2006.01)
*A61M 37/00* (2006.01)
*A61M 1/00* (2006.01)
*A61M 5/00* (2006.01)

(52) U.S. Cl.
USPC ........... 604/135; 604/131; 604/134; 604/151; 604/207

(58) Field of Classification Search
USPC .................................. 604/131, 151, 207, 134
See application file for complete search history.

(56) References Cited

U.S. PATENT DOCUMENTS

| | | | | |
|---|---|---|---|---|
| 5,569,190 A | * | 10/1996 | D'Antonio | 604/72 |
| 5,591,136 A | * | 1/1997 | Gabriel | 604/211 |
| 5,820,602 A | * | 10/1998 | Kovelman et al. | 604/187 |
| 6,348,043 B1 | * | 2/2002 | Hagen et al. | 604/151 |
| 2003/0158523 A1 | * | 8/2003 | Hjertman et al. | 604/207 |

(Continued)

FOREIGN PATENT DOCUMENTS

| | | |
|---|---|---|
| EP | 0334349 A1 | 9/1989 |
| EP | 1084763 A2 | 3/2001 |

(Continued)

*Primary Examiner* — Theodore J Stigell
*Assistant Examiner* — Ian Holloway
(74) *Attorney, Agent, or Firm* — Hoffman & Baron, LLP

(57) ABSTRACT

The invention relates to a device (1) for delivering two predetermined doses of a product (3), comprising: —a container (2) for containing said product, said container having a distal end (2*d*) through which the product is delivered under the distal pressure of a piston, —a pusher (7) movable with respect to said container for causing said piston (4) to move in the distal direction from an initial position, in which none of said product has been expelled to a first position, in which a first dose of said product has been expelled, and to a second position, in which a second dose of said product has been expelled, —a holder body (15) receiving said container and said pusher (7), —biasing means (22) for urging said pusher (7) in the distal direction, from the initial to the first position, and to the second position, —first and second retaining means (9, 11, 19) for maintaining said pusher (7) in said initial position, and in said first position, —first and second actuation means (18) to deactivate said first and second retaining means (9, 11, 19), characterized in that said first and/or second actuation means (18) are at least rotationally displaceable, said rotation causing at least part of the deactivation of said first and/or second retaining means (9, 11, 19).

24 Claims, 14 Drawing Sheets

(56) References Cited

U.S. PATENT DOCUMENTS

Figure 1:
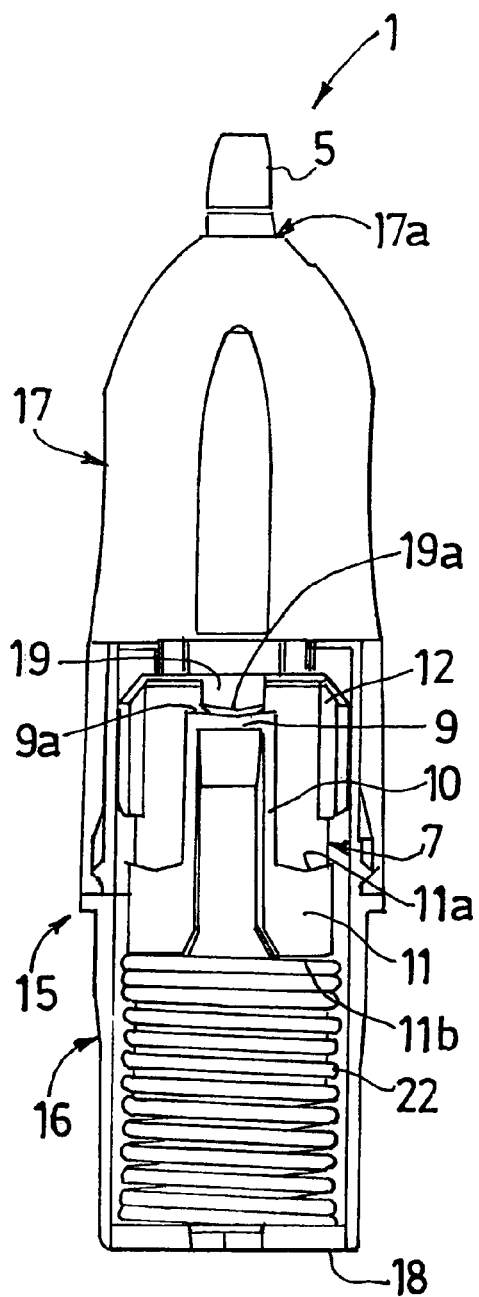

2007/0233001 A1* 10/2007 Burroughs et al. ............ 604/131
2007/0299390 A1* 12/2007 Bellhouse et al. .............. 604/70
2009/0283547 A1* 11/2009 Harrold ......................... 222/256

FOREIGN PATENT DOCUMENTS

| | | |
|---|---|---|
| FR | 2793707 A1 | 11/2008 |
| FR | 2793708 A1 | 11/2008 |
| WO | 2004028703 A2 | 4/2004 |

* cited by examiner

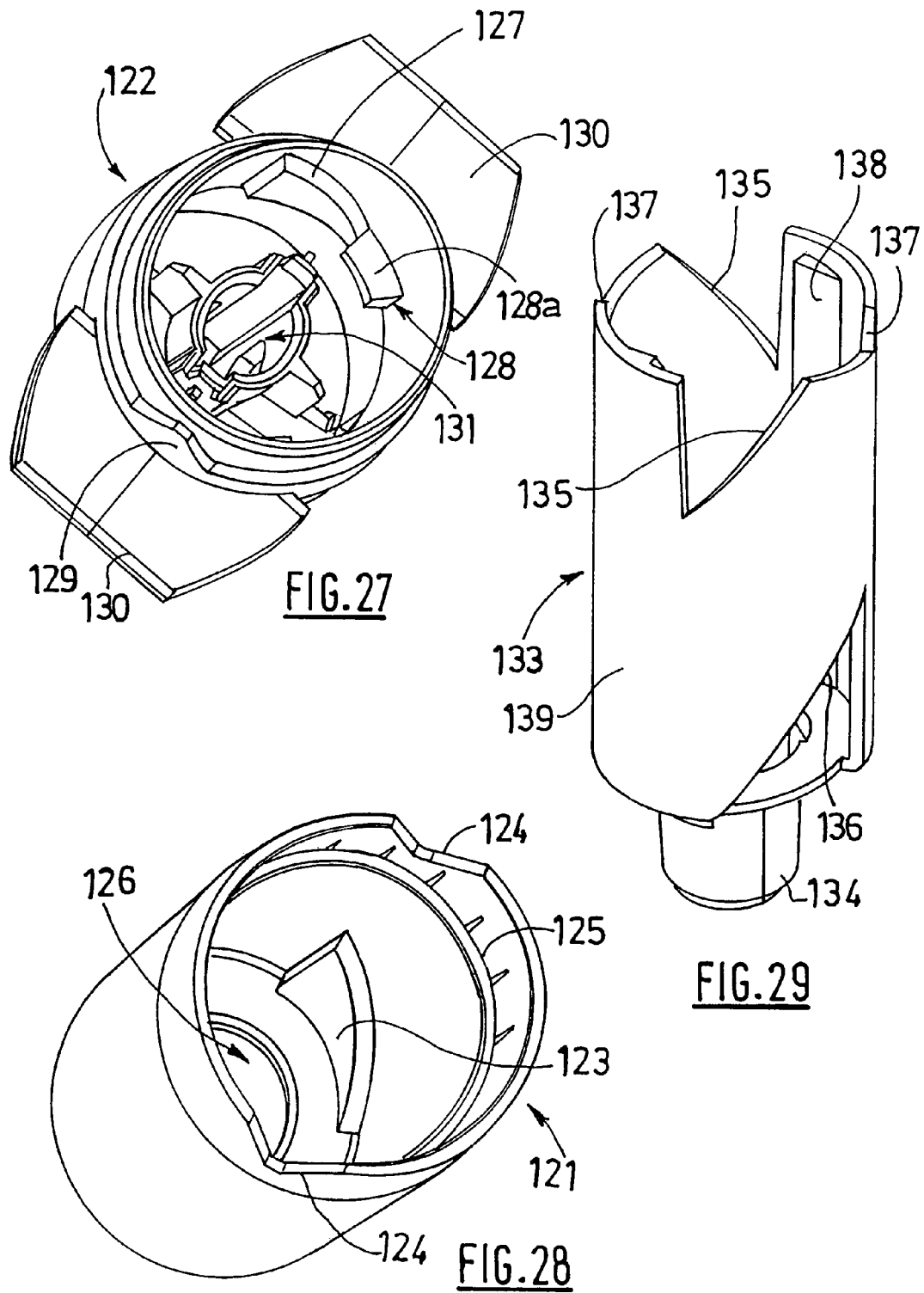

DEVICE FOR AUTOMATIC DELIVERY OF SUCCESSIVE DOSES OF PRODUCT

The present invention relates to a device for delivering successively at least two predetermined doses of a product, for instance a medicinal product. The invention is especially applicable to a nasal spray device making it possible to deliver successively two doses, one for each nostril.

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of delivery or administration of the product, and the "proximal direction" is to be understood as meaning the opposite direction to the direction of delivery or administration of the product.

Nasal spray devices, based on the general structure of a syringe, having means for dividing the travel of a pusher intended to cause the ejection of the product into two doses, are known: usually, in these devices, the pusher is coupled to a piston that forces the product to be ejected, for instance through a spray nozzle. These nasal spray devices allow the delivery of two successive doses of a product. Such nasal spray devices are described for example in the application WO2004/028703 of the applicant.

Nevertheless, in such nasal spray devices, the user has to manually press on the pusher with his fingers and/or hand and maintain the pressure all along the pusher displacement. In consequence, it is the user who applies the necessary force for pushing the piston within the container where the product to be delivered is stored. This force must be important enough to both displace the pusher and create the spray within the spray nozzle. In addition, since this spray is created manually, it is not always reproducible: the droplets size, the length of the spray, the angle of the spray, may vary from one dose to the other and/or from one user to another one.

In consequence, the existing nasal spray devices have the drawbacks of not being reproducible and neither very easy to manipulate: since the user has to apply and maintain a high force on the pusher in order to create the spray, he can not control the parameters of the spray such as the droplets size, the angle of the spray, etc. . . .

Document FR 2 793 707 discloses a device for the delivery of at least two doses of product, the device being actuated by means of a lateral button on which the user has to exert a radial force.

Document U.S. Pat. No. 6,348,043 discloses a multi-dose infusion pump for delivery of different doses of product directly within the vein of a patient in a continuous manner.

FR 2 793 708 A1 discloses a device for the delivery of at least two doses, wherein the administration of the product is actuated by a preloaded delivery device.

EP 0 334 349 A1 discloses a device for the successive delivery of two doses of product.

There is therefore a need for a device that would allow the successive delivery of at least two predetermined doses, in a very reproducible way, and that would be very simple to manipulate for the user.

The present invention meets this need by providing a new device which is easy to manipulate and allows the automatic and reproducible successive delivery of two predetermined doses with minimal intervention from the user.

The present invention proposes a device for the successively delivery of at least two predetermined doses of a product, comprising:

a container defining a reservoir for containing the product to be delivered, said container having an open proximal end, and a distal end defining an outlet port in combination with said reservoir and through which the product may be delivered, a piston movable with respect to said reservoir, the distal movement of said piston causing at least part of the product to be expelled from said container, a pusher movable with respect to said container for causing said piston to move in the distal direction successively from an initial position, in which none of said product has been expelled to a first position, in which a first dose of said product has been expelled, and to a second position, in which a second dose of said product has been expelled, a holder body, intended to receive at least part of said container and said pusher, first biasing means designed for tending to urge said pusher in the distal direction, at least from the initial position to the first position, first retaining means designed for maintaining said pusher in said initial position, first actuation means designed for deactivating said first retaining means and allowing the distal displacement of said pusher at least from the initial to the first positions second biasing means designed for tending to urge said pusher in the distal direction from the first position to at least said second position, second retaining means designed for maintaining said pusher in said first position, second actuation means designed for deactivating said second retaining means and allowing the distal displacement of said pusher at least from the first to the second positions, characterized in that said first and/or second actuation means are at least rotationally displaceable, said rotation causing at least part of the deactivation of said first and/or second retaining means.

The device of the invention allows a very reproducible spray: Indeed, the spray created with the device of the invention is totally independent from the user and especially totally independent from a force exerted by the user. The quality of the spray is therefore improved: the droplets size, the length of the spray, the angle of the spray are reproducible from one dose to the other, regardless from the intensity of the force exerted by the user on the pusher or on any element coupled to said pusher.

Moreover, the device of the invention is very friendly. The administration of the product is very precise.

The device of the invention may also be used as an oral spray for delivering two or more than two successive doses of product.

In embodiments of the invention, said first and/or second actuation means are additionally at least axially displaceable, the combination of said rotation and said axial displacement causing the deactivation of said first and/or second retaining means.

In embodiments of the invention, said first and second actuation means are confounded. For example, the first actuation means and the second actuation means are made of one single element or actuation device. The delivery device of the invention is therefore easier to manufacture and easier to handle and to operate by the user.

In embodiments of the invention, said first and second biasing means are confounded. The delivery device of the invention is therefore simple.

In an embodiment of the invention, said pusher is able to rotate with respect to at least part of said holder body, said first retaining means being deactivated by a first rotation of said pusher with respect to said part of said holder body.

Preferably, said second retaining means are deactivated by a second rotation of said pusher with respect to said part of said holder body.

In a further embodiment of the invention, said first retaining means comprise at least a first relief surface formed on the outer wall of said pusher and at least a first complementary relief surface formed on the inner wall of said part of said holder body, said first and first complementary relief surfaces cooperating so as to be engaged in one another in the initial position and disengaged from one another after said first rotation of said pusher with respect to said part of said holder body.

In a further embodiment of the invention, said second retaining means comprise at least a second relief surface formed on the outer wall of said pusher and at least a second complementary relief surface formed on the inner wall of said part of said holder body, said second relief surface and second complementary relief surface cooperating so as to be engaged in one another in the first position and disengaged from one another after said second rotation of said pusher with respect to said part of said holder body.

Preferably, said first relief surface and/or said first complementary relief surface and/or said second relief surface and/or said second complementary relief surface are chosen in the group comprising a radial stop, a radially projecting surface, a cam, a recess.

In an embodiment of the invention, said holder body comprises at least two parts, a proximal part and a distal part which are able to rotate one with respect to the other, said distal part being coupled to said container, said pusher being able to rotate with respect to said proximal part, said proximal part forming at least in part said rotationally activable first and/or second actuation means, said device comprising guiding means for preventing said pusher to rotate with respect to said distal part when said proximal part is rotated by the user and that said pusher moves from its initial position to its first position, and then from its first position to its second position.

Preferably, said guiding means are partly formed on said pusher and partly formed on said distal part of said holder body.

Preferably, said guiding means comprises at least a longitudinal cam formed on the pusher and at least a longitudinal leg formed on said distal part of said holder body, said longitudinal leg being engaged into said longitudinal cam at least from the initial position to said second position of said pusher.

In an embodiment of the invention, the device comprises two second complementary relief surfaces, one being laterally located on one side of said first relief surface and the other one being laterally located on the other side of said first relief surface.

In an embodiment of the invention, the device comprises two second relief surfaces, one being laterally located on one side of said first relief surface and the other one being laterally located on the other side of said first relief surface.

Preferably, said first relief surface and first complementary relief surface and/or said second relief surface and second complementary relief surface have triangular respectively complementary shapes.

In a further embodiment of the invention, the device further comprises automatic rotating means for causing the rotation of said pusher with respect to said holder body when said first and/or second actuation means are axially activated.

Preferably, said first and/or second actuation means comprise at least one button, in which for example is received said pusher, said button being received in said holder body, said button being movable in translation and in rotation within said holder body, said button comprising a proximal pressing surface, said proximal pressing surface extending outwardly and proximally from said holder body.

In an embodiment of the invention, said automatic rotating means comprise at least one first ramp provided on said button and at least one second ramp provided on said holder body, said first and second ramps cooperating with each other so as to cause the rotation of said button with respect to said holder body, when a distal force is exerted on, or released from, said proximal pressing surface of said button.

In an embodiment of the invention, said automatic rotating means comprise at least one first rotation stop and one second rotation stop provided on said pusher or on said button and one rotation abutment respectively located on said button or on said pusher, said first and second rotation stops and said rotation abutment successively cooperating with each other so as to cause the rotation of said pusher or button with respect to said holder body, when said button rotates when a distal force is exerted on its said proximal pressing surface of said button.

Preferably, said second rotation stop is elastically deformable to pass over said rotation abutment after said first position is reached by said pusher and to abut against said rotation abutment between first and second positions.

In an embodiment of the invention, said first and/or second biasing means comprise at least one helical spring.

In a further embodiment of the invention, the device further comprises third retaining means for maintaining said pusher in said second position.

Figure 2:
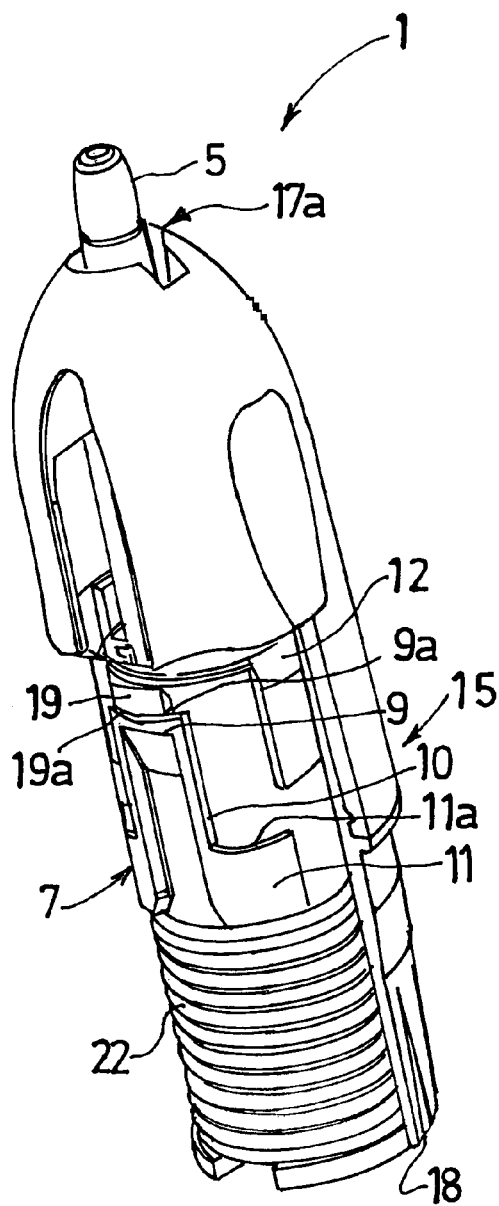
Figure 3:
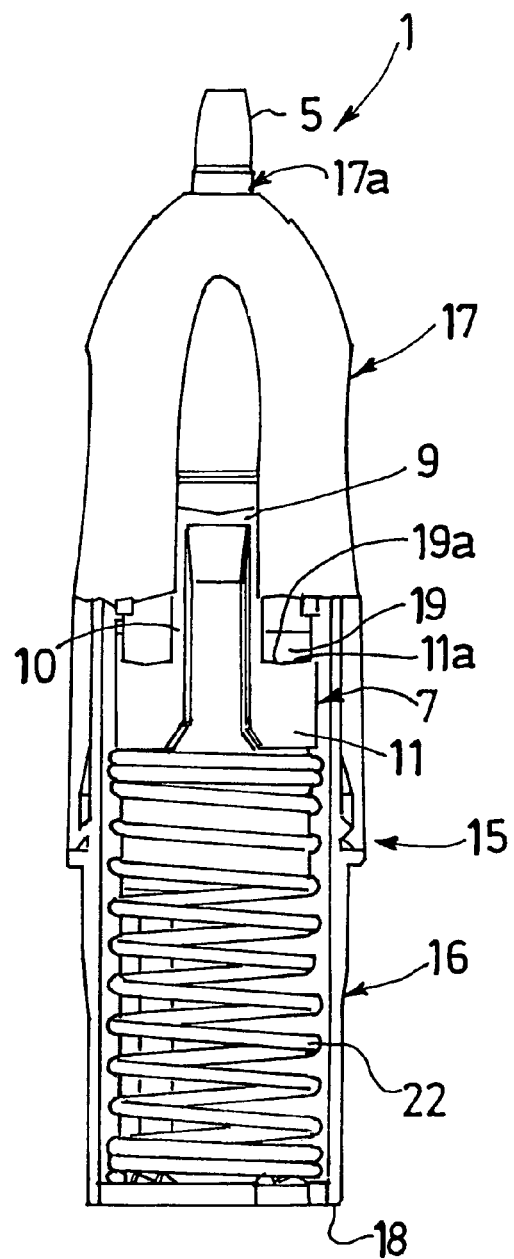
Figure 4:
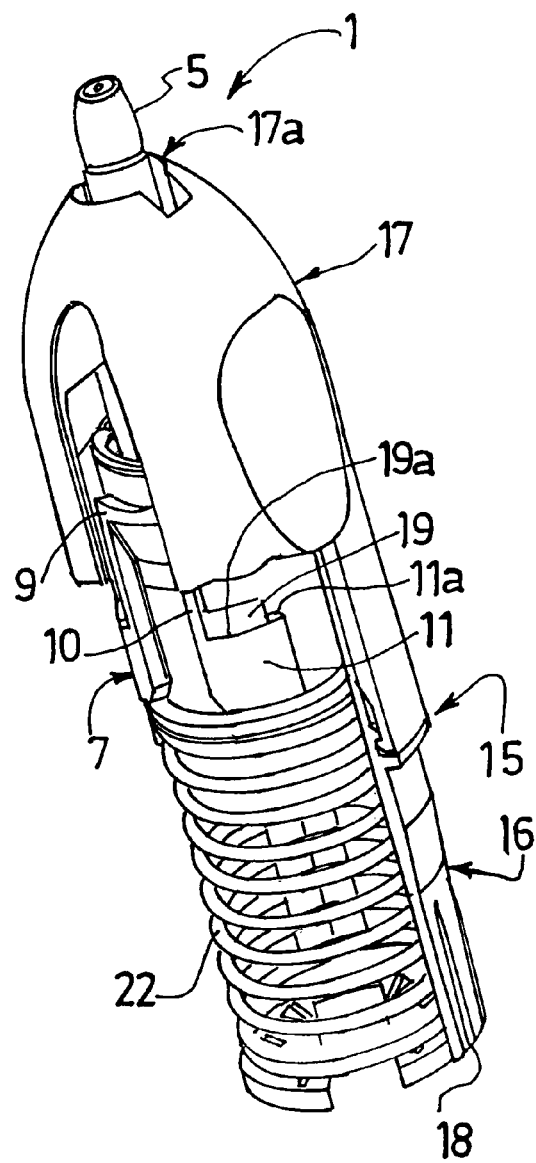
Figure 5:
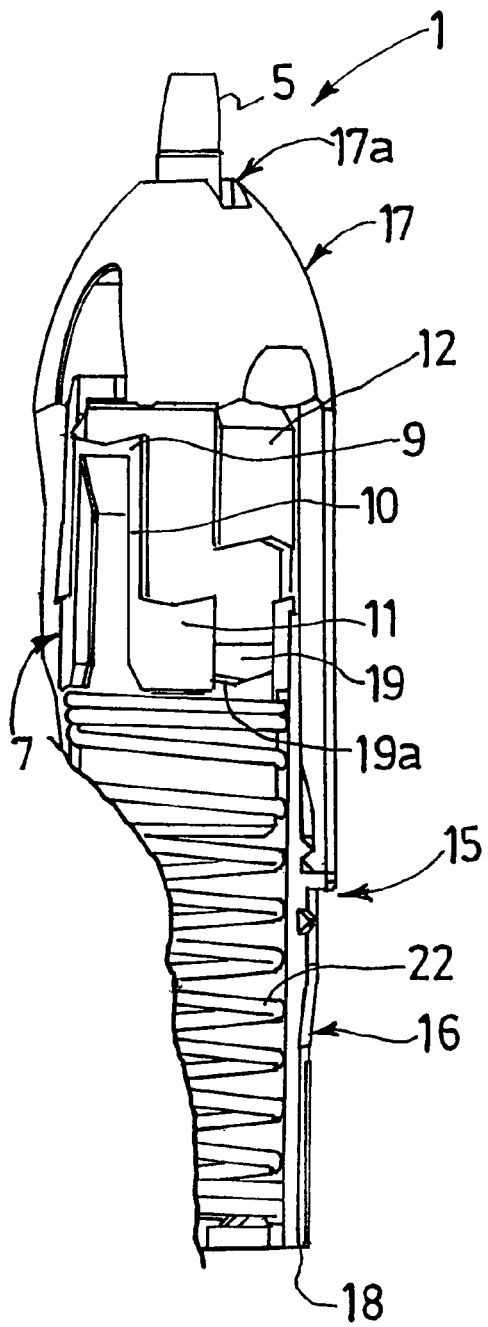
Figure 6:
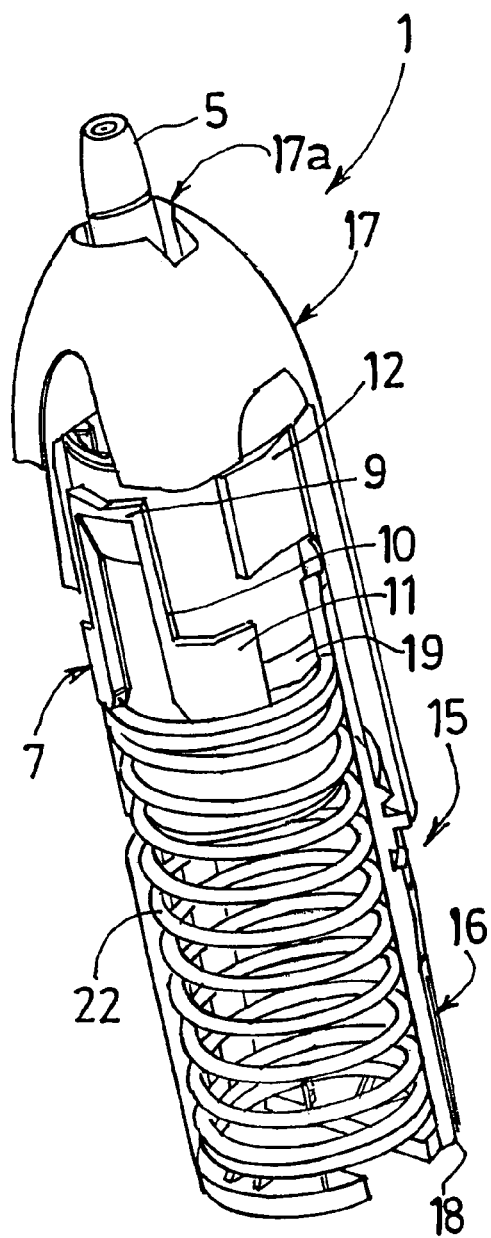
Figure 7:
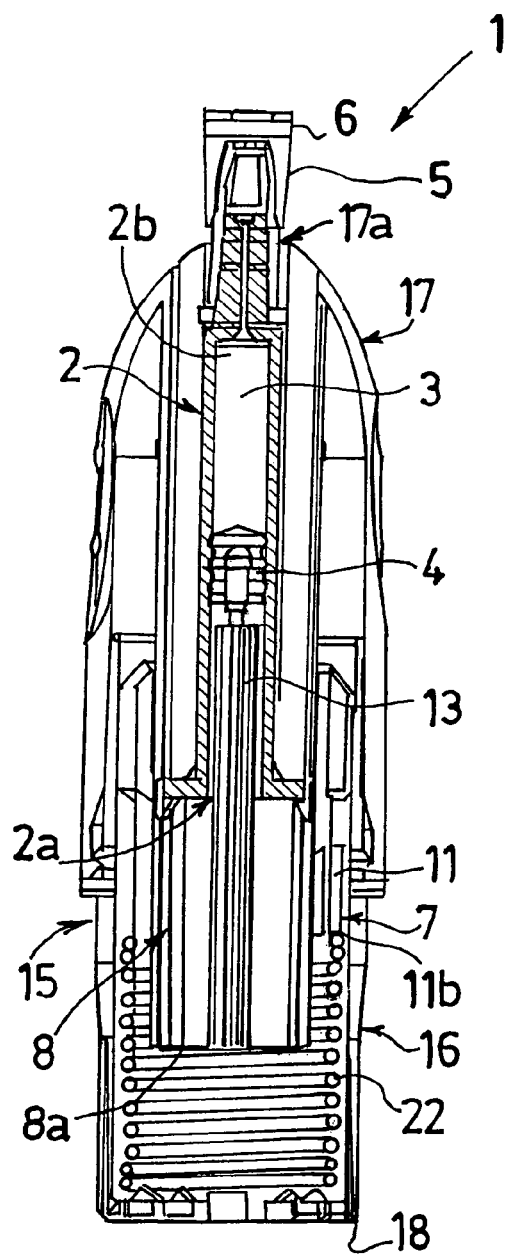
Figure 8:
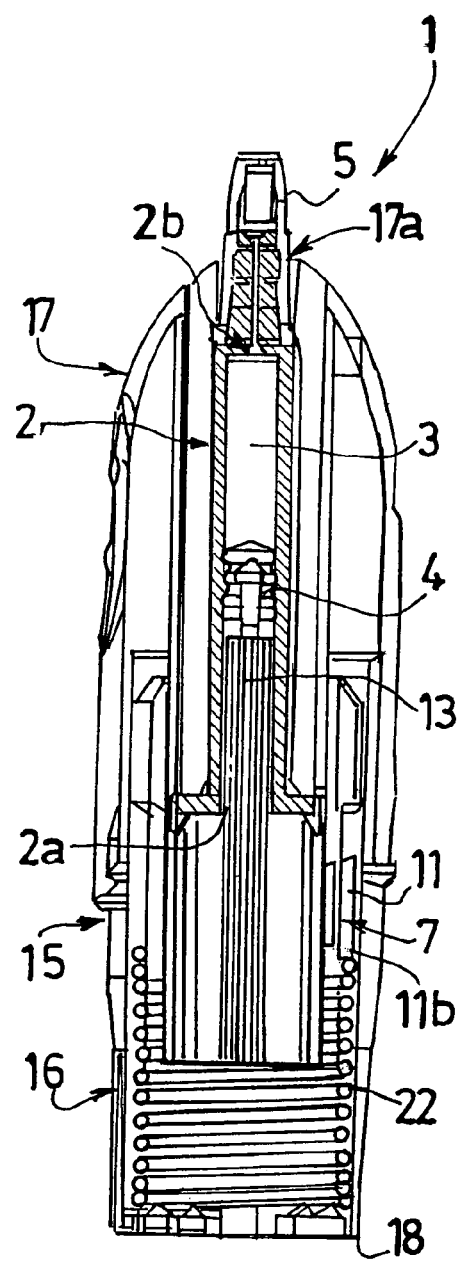
Figure 9:
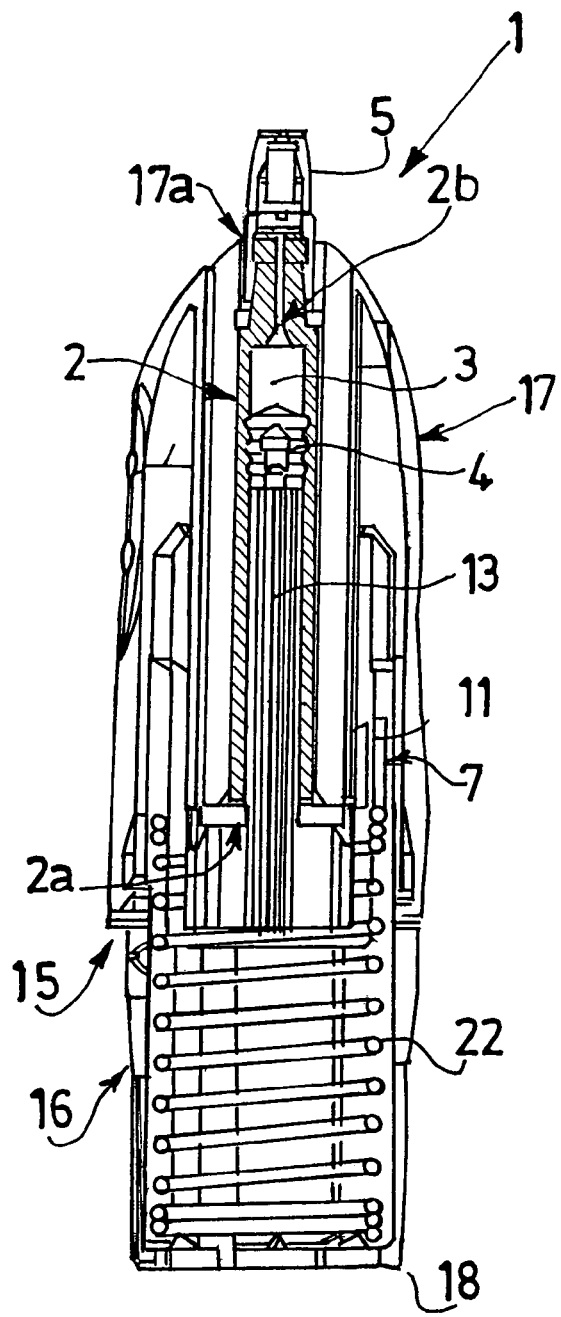
Figure 10:
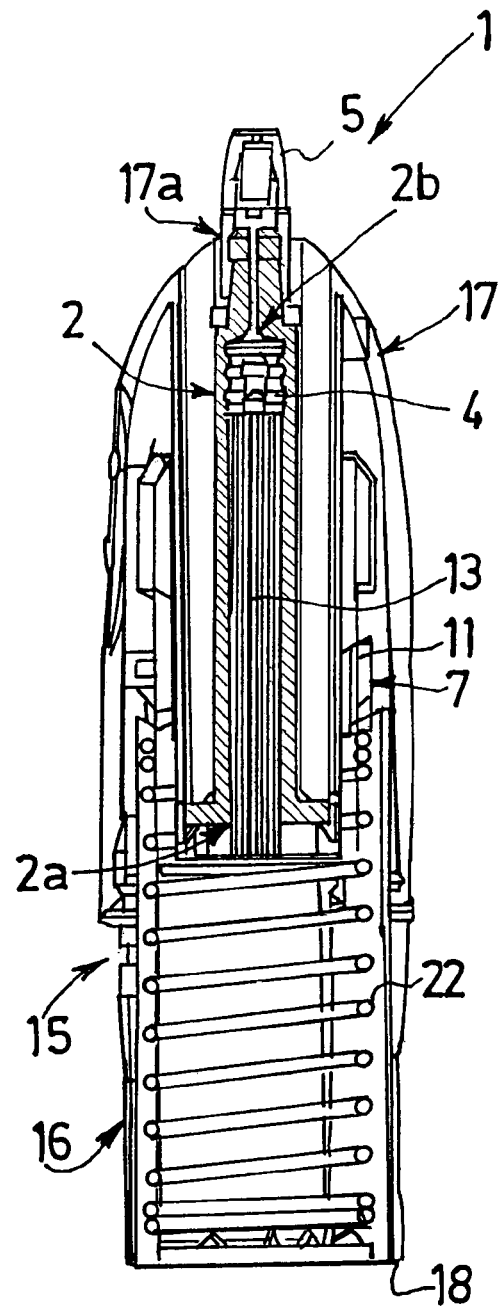
Figure 11:
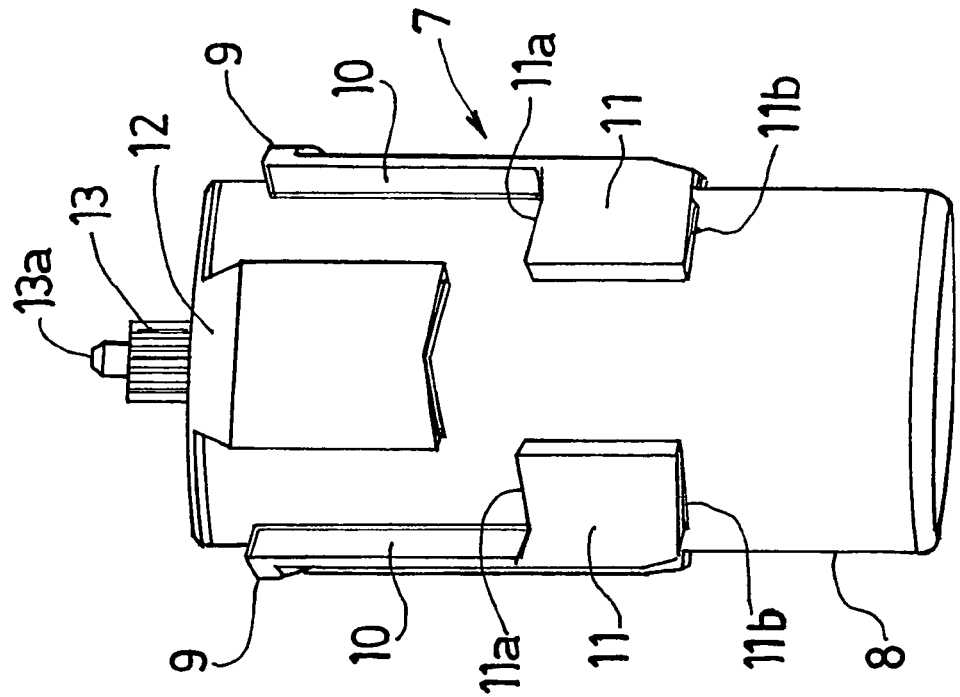
Figure 12:
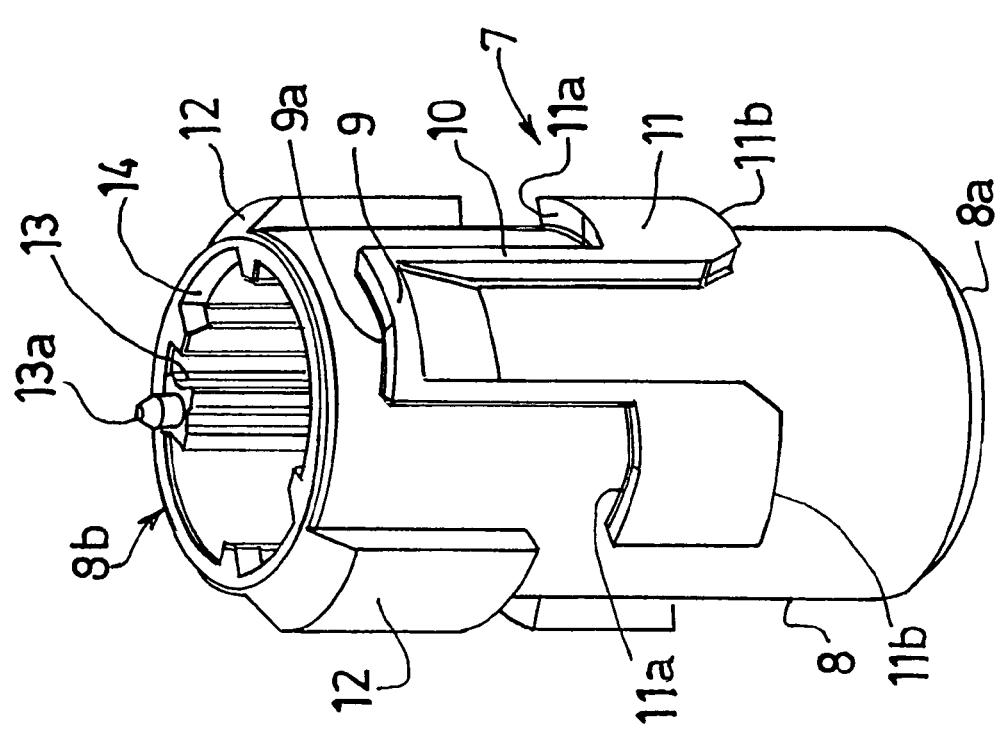
Figure 14:
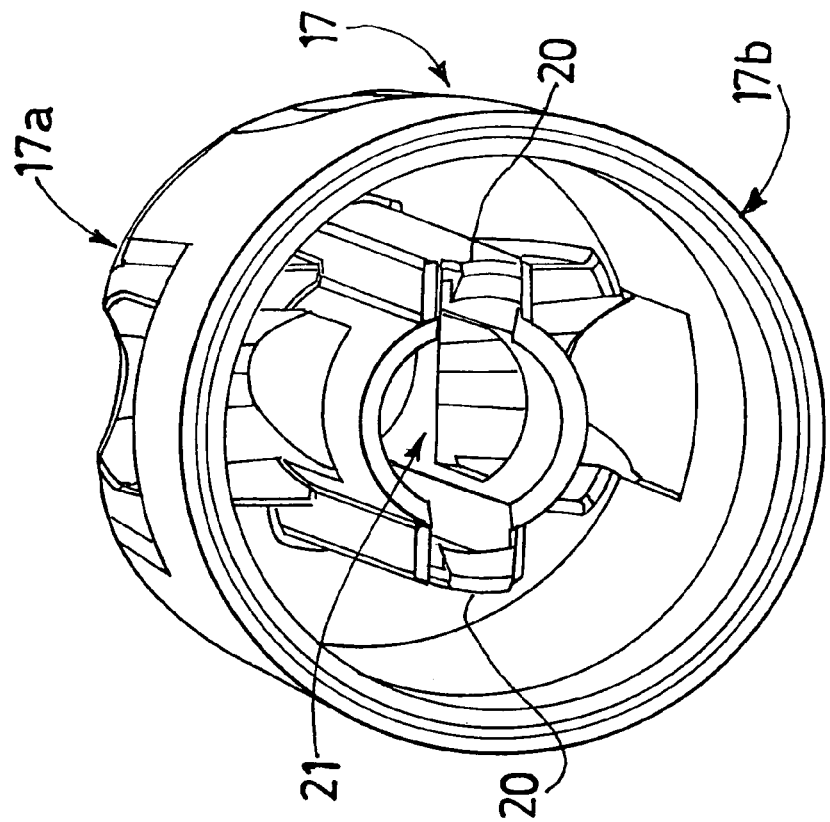
Figure 13:
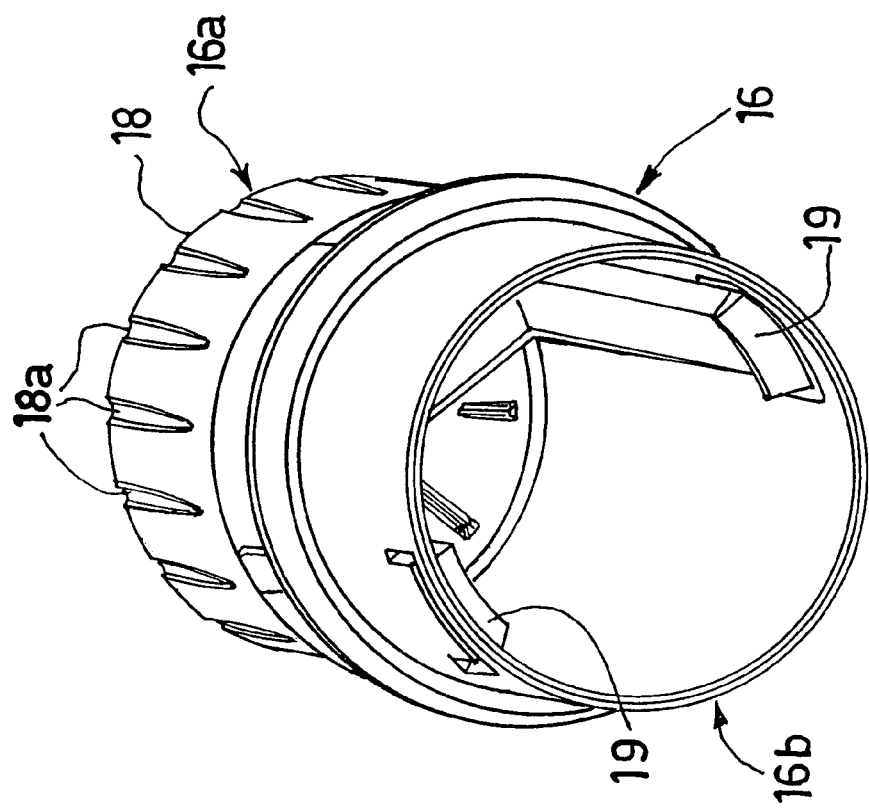
Figure 15:
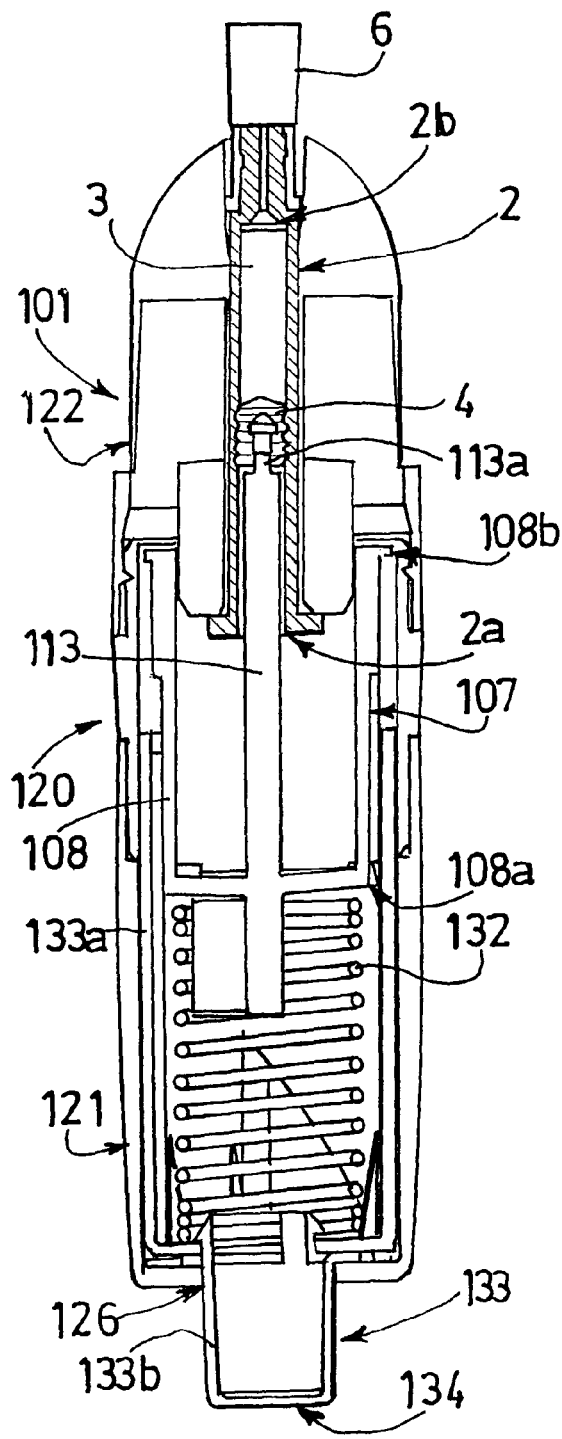
Figure 16:
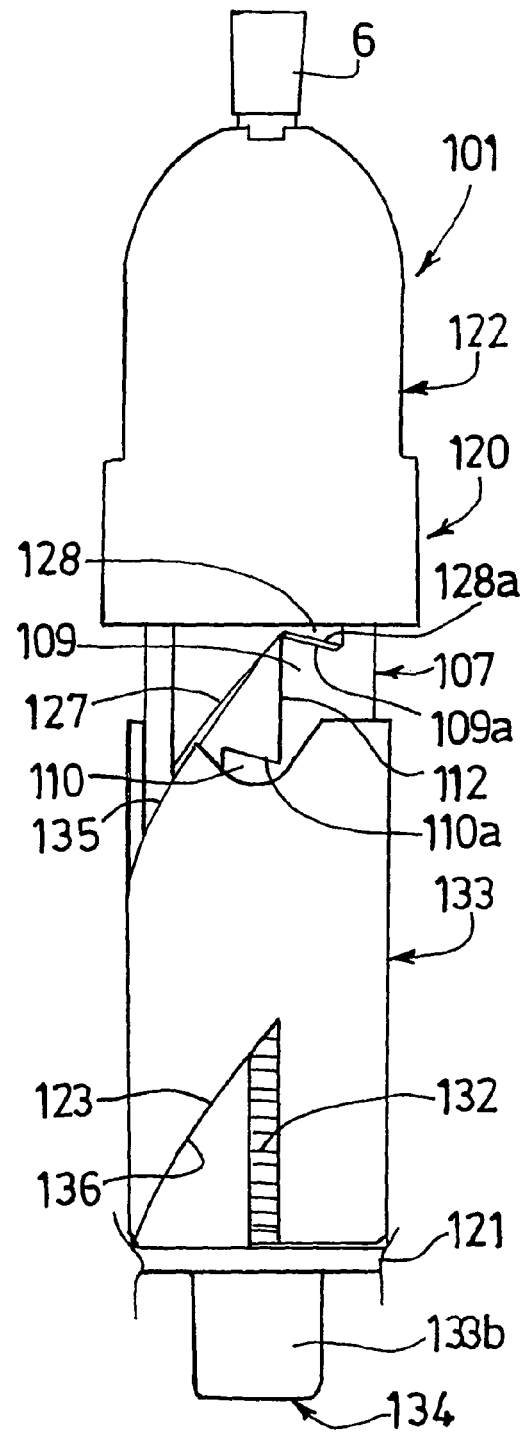
Figure 17:
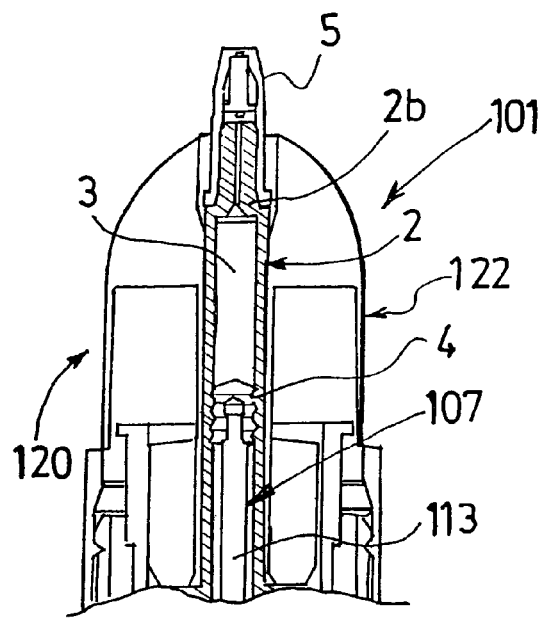
Figure 18:
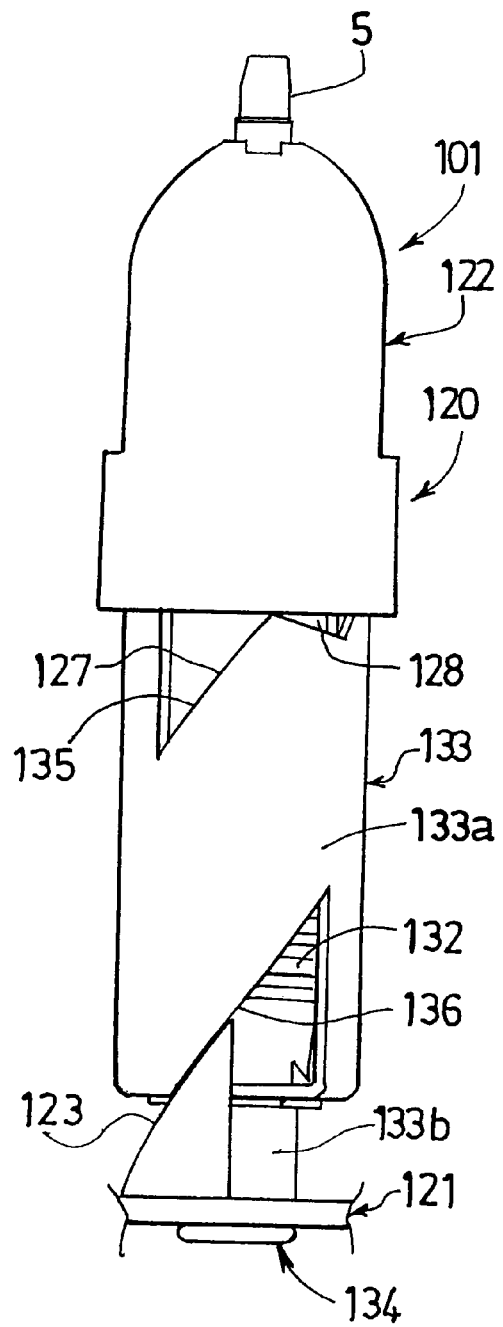
Figure 19:
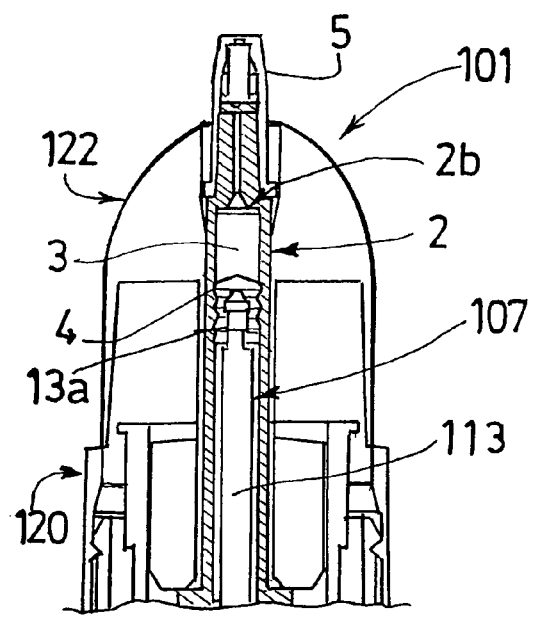
Figure 20:
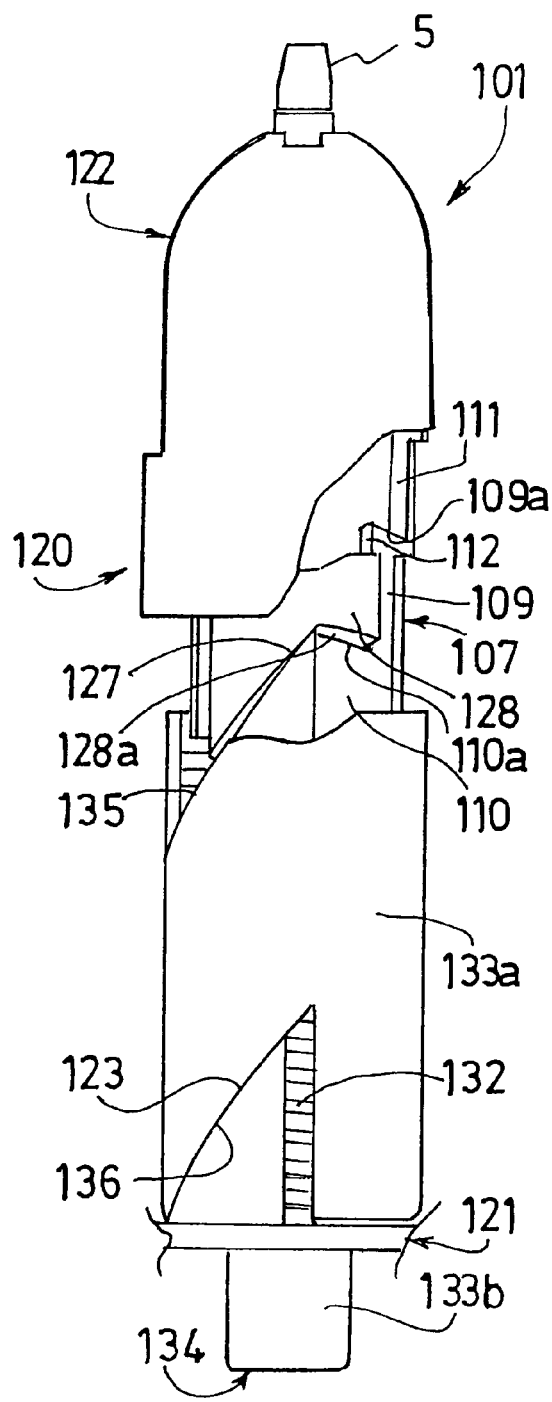
Figure 21:
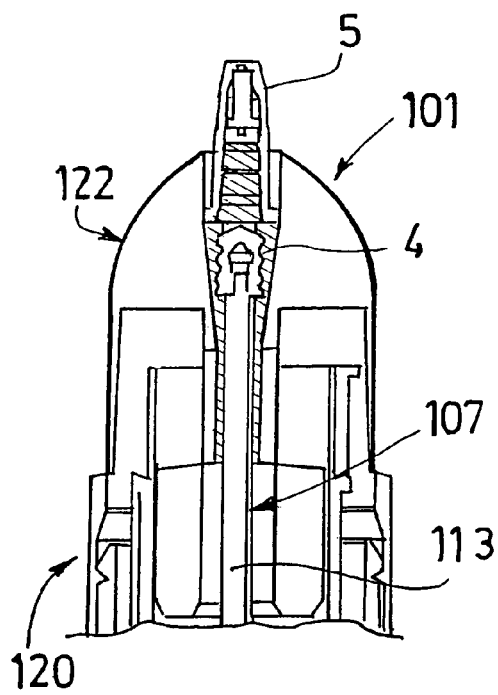
Figure 22:
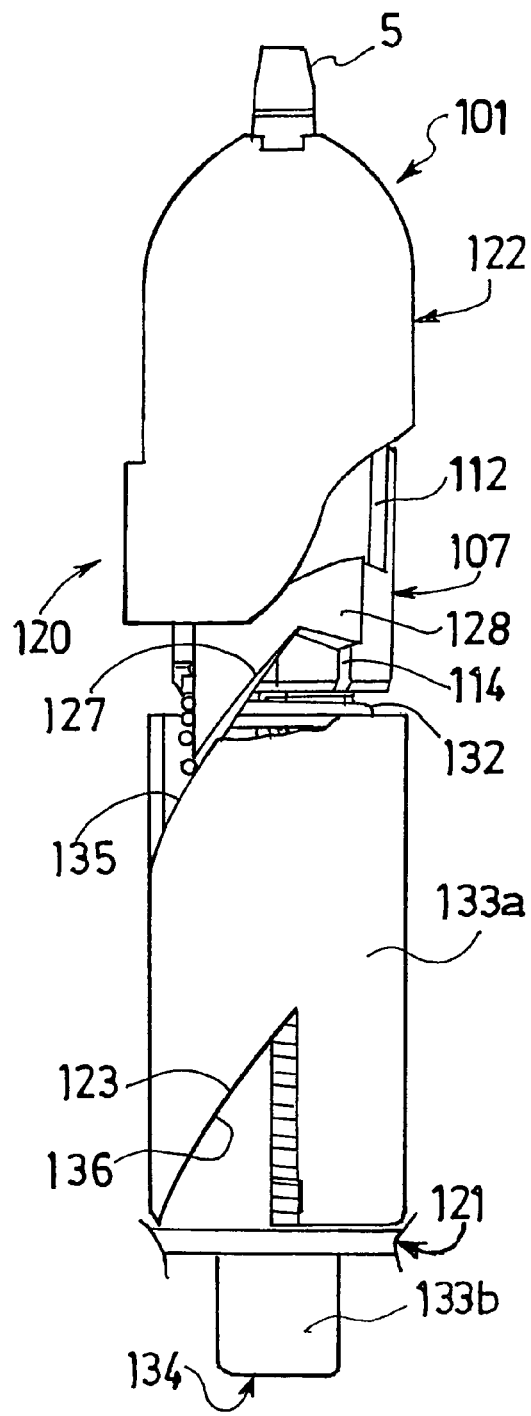
Figure 24:
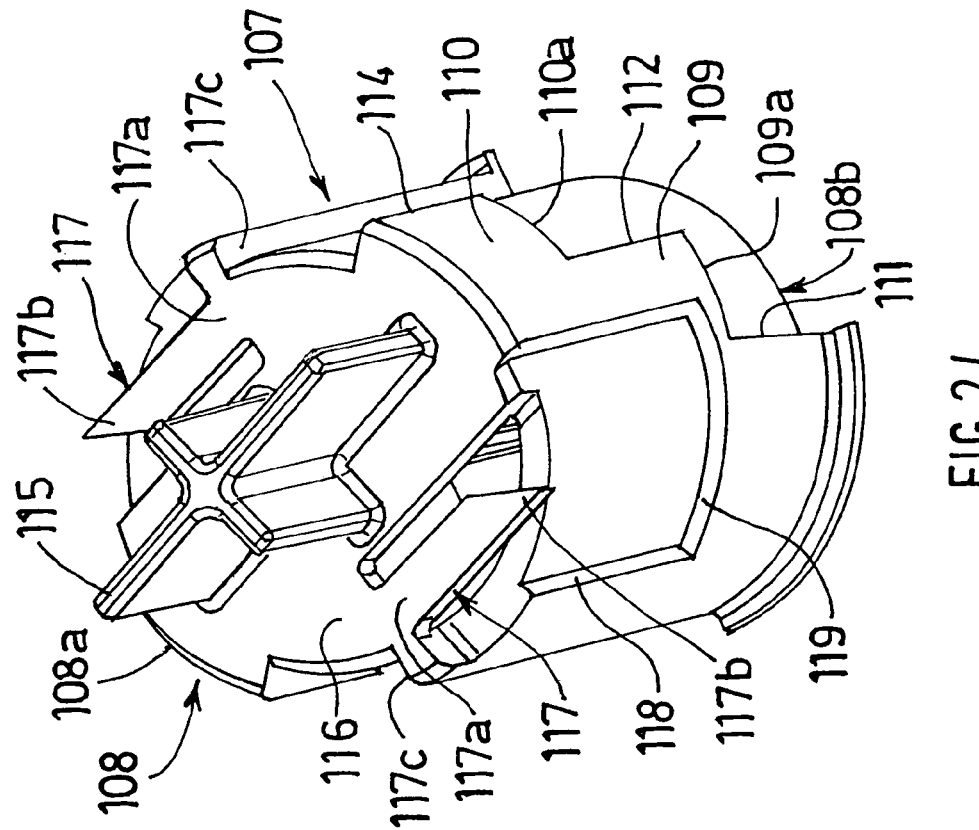
Figure 23:
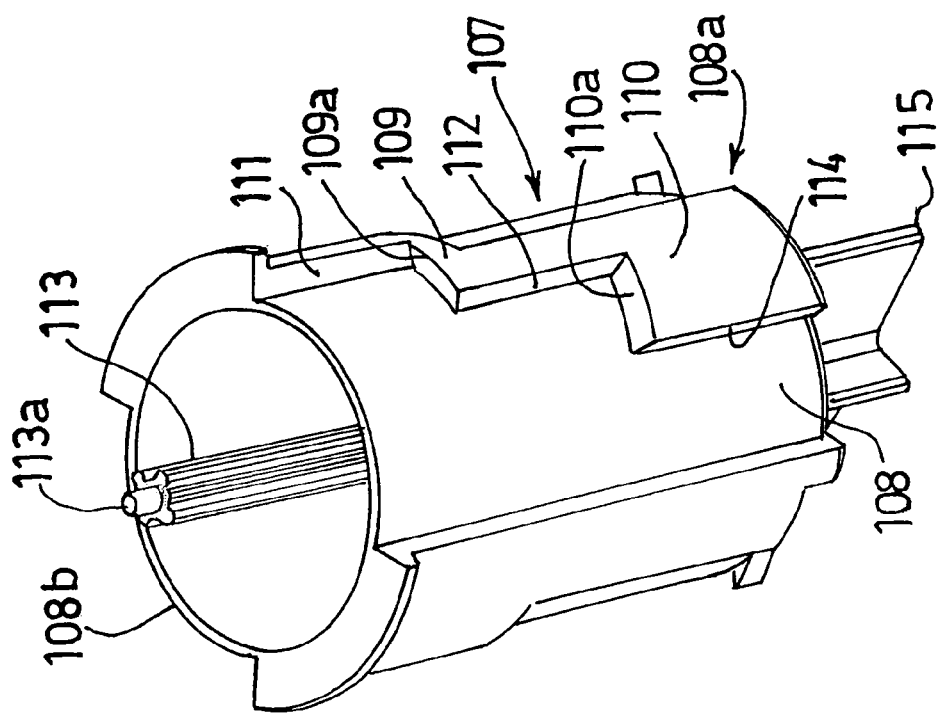
Figure 25:
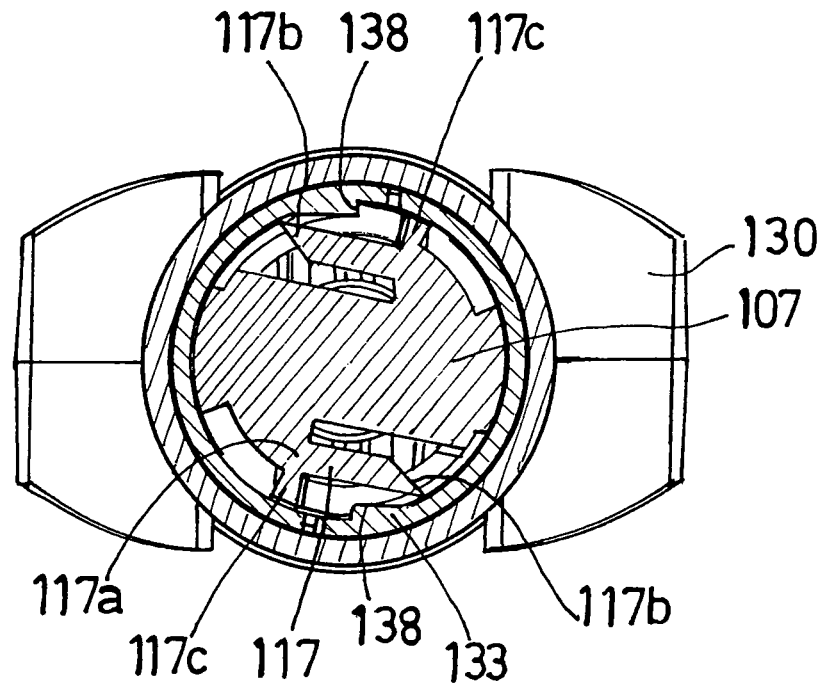
Figure 26:
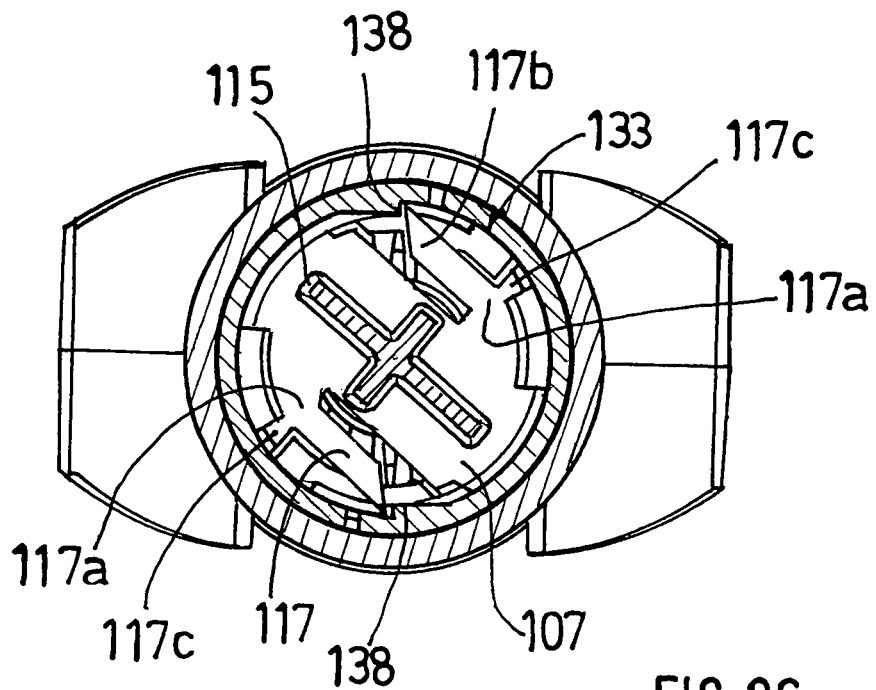

The device of the invention will now be further described in reference to the following description and attached drawings in which:

FIG. 1 is a partial cross section side view of a device according to the invention in the initial position, FIG. 2 is a perspective view of the device of FIG. 1, FIG. 3 is a partial cross section side view of the device of FIG. 1 in the first position, FIG. 4 is a perspective view of the device of FIG. 3, FIG. 5 is a partial cross section side view of the device of FIG. 1 in the second position, FIG. 6 is a perspective view of the device of FIG. 5, FIG. 7 is a cross section view of the device of FIG. 1 before use, FIGS. 8 to 10 are cross section views of the device of FIG. 1 respectively in the initial, first and second positions, FIG. 11 is a perspective view of the pusher of the device of FIG. 1, FIG. 12 is a side view of the pusher of FIG. 11, FIG. 13 is a perspective view of the proximal part of the holder body of the device of FIG. 1, FIG. 14 is a perspective view of the distal part of the holder body of the device of FIG. 1, FIG. 15 is a cross section view of a second embodiment of the device of the invention in the initial position, FIG. 16 is a partial cross section side view of the device of FIG. 15, FIG. 17 is a partial cross section view of the device of FIG. 15 in the initial position, FIG. 18 is a partial cross section side view of the device of FIG. 15 in the initial position, FIG. 19 is a partial cross section view of the device of FIG. 15 in the first position, FIG. 20 is a partial cross section side view of the device of FIG. 15 in the first position, FIG. 21 is a partial cross section view of the device of FIG. 15 in the second position, FIG. 22 is a partial side view of the device of FIG. 15 in the second position, FIG. 23 is a perspective view of the pusher of the device of FIG. 15, seen from the top, FIG. 24 is a perspective view of the pusher of the device of FIG. 15, seen from the bottom, FIG. 25 is a cross section view from below of the device of FIG. 15 between the initial and first positions, FIG. 26 is a cross section view from below of the device of FIG. 15 between the first and second positions, FIG. 27 is a perspective view of the distal part of the holder body of the device of FIG. 15, seen from the bottom, FIG. 28 is a perspective view of the proximal part of the holder body of the device of FIG. 15, seen from the top, FIG. 29 is a perspective view of the button of the device of FIG. 15.

In reference to FIGS. 1-14 is represented a first embodiment of a device 1 according to the invention, for the delivery of at least two predetermined doses of a product.

On FIG. 1 is represented a device 1, comprising a pusher 7, a holder body 15, receiving said pusher 7, said holder body 15 comprising two parts, a proximal part 16 and a distal part 17. The holder body 15 also receives a helical spring 22.

As appears more clearly from FIG. 7, the device 1 also comprises a container 2 defining a reservoir for containing the product 3 to be delivered. The container 2 is received within said holder body 15. The container 2 has an open proximal end 2a and a distal end 2b which defines an outlet port in combination with said reservoir and through which the product 3 may be expelled.

The device 1 of FIG. 7 further comprises a piston 4, movable within said container 2. The distal movement of said piston 4 is intended to cause at least part of the product 3 to be expelled from said container 2 via the outlet port located at the distal end 2b of said container 2.

At its distal end 2b, the container 2 is provided with a nozzle 5 through which the product 3 is expelled as droplets.

As will now appear more clearly from FIGS. 11 and 12, the pusher 7 has the global shape of a cylinder 8 having a closed proximal end 8a and an open distal end 8b. The cylinder 8 is provided on its outer wall with projecting shapes (9, 10, 11, 12) protruding outwardly. In particular, the cylinder 8 is provided in its distal region with two first projecting shapes 9, diametrically opposed (see FIG. 12): each of these two first projecting shapes 9 is adjacent to two second projecting shapes 11, proximally spaced from said first projecting shape 9, one being laterally located on one side of said first projecting shape 9, and the other being laterally located on the other side of said first projecting shape 9. Each first projecting shape 9 is connected to its respective two adjacent second projecting shapes 11 by a longitudinal projecting ridge 10.

The respective distal faces of these first and second projecting shapes (9, 11) form relief surfaces (9a, 11a), the function of which will be explained later.

The proximal faces 11b of the second projecting shapes 11 form radial abutments for the distal end of the spring 22, as shown on FIG. 1.

The cylinder 8 is further provided at the distal end of its outer wall with two third projecting shapes 12, extending longitudinally in the proximal direction and which are diametrically opposed.

Extending from the inner face of the closed proximal end 8a of the cylinder 8 (see FIG. 7) is a piston rod 13, the distal end 13a of which protrudes outside said cylinder 8, as shown on FIG. 11. The distal end 13a of said piston rod 13 is intended to be coupled with the piston 4, as shown on FIGS. 7 to 10.

On its inner wall, the cylinder 8 is providing with two longitudinal cams 14 which are diametrically opposed.

On FIGS. 13 and 14 are shown respectively the proximal part 16 and the distal part 17 of the holder body 15 of FIG. 1.

In reference to FIG. 13, the proximal part 16 of the holder body 15 has the general shape of a sleeve having a closed proximal end 16a and an open distal end 16b. As will appear later, the closed proximal end 16a may be provided with regularly spaced grooves 18a in order to form a gripping part 18 of the device 1 for the user.

The inner wall of the proximal part 16 is provided at its distal end 16b with two inwardly protruding stops 19, which are diametrically opposed. The proximal face 19a of said stops (visible on FIGS. 1-5) form relief surfaces, the function of which will be explained later.

In reference with FIG. 14, the distal part 17 of the holder body 15 has the global shape of a sleeve having an open proximal end 17b which is intended to fit on the distal end 16b of the proximal part 16. The two parts (16, 17) of the holder body 15 are connected to each other so that the proximal part 16 is able to rotate with respect to the distal part 17.

The diameter of the cross section of the distal part 17 shrinks in the distal direction until the distal end 17a (visible on FIGS. 1-10 and 14) which forms an opening for the nozzle 5 to pass there through. The opening formed by the distal end 17a of the distal part 17 is continued within the proximal part 17 by an internal skirt 21 extending in the proximal direction. Said internal skirt 21 is intended to receive the distal region of the container 2. As can be seen on FIG. 14, the internal skirt 21 is provided on its outer wall with two diametrically opposed longitudinal legs 20 extending along the length of said internal skirt 21.

The operation of the device 1 will now be described in reference to FIGS. 1 to 10.

Before use, the device 1 is provided to the user in the position shown on FIG. 7 with a cap 6 provided on the nozzle 5 in order to keep it clean and avoid all accidental leakage of any product 3.

After removal of the cap 6, the device 1 is ready to be used and is in the initial position, shown on FIGS. 1, 2 and 8. In this initial position, the spring 22 is at least partially compressed. The distal end of said spring 22 is bearing against the proximal faces 11b of the second projecting faces 11 and the proximal end of said spring 22 is bearing against the inner face of the closed proximal end 16a of the proximal part 16 of the holder body 15.

As appears clearly from FIGS. 1 and 2, the distal face of the first projecting shape 9 and the proximal face of the stop 19 form respectively a first relief surface 9a and a first complementary relief surface 19a which are engaged in each other thereby constituting first retaining means of the pusher 7 in its initial position. Said first relief surface 9a and said first complementary relief surface 19a have, in this example, triangular complementary shapes.

In this initial position, as shown on FIG. 8, the piston 4 has not moved from its position before use and none of the product 3 has been expelled yet. Moreover, the longitudinal legs 20 (see FIG. 14) of the internal skirt 21 of the distal part 17 of the holder body 15 are engaged in the longitudinal cams 14 (see FIG. 11) of the pusher 7.

In order to proceed with the delivery of the first predetermined dose of the product 3, the user seizes for example the distal part 17 of the holder body 15 of the device 1 with one hand and he grips the gripping part 18 of the proximal part 16 of the holder body 15 with the other end, rotating the gripping part 18 with respect to the distal part 17 clockwise or counter clockwise indifferently.

By rotating the gripping part 18 of the holder body 15, the user causes the first relief surface 9a to disengage from the first complementary relief surface 19a, freeing the pusher 7, which is pushed distally under the force of the spring 22 which tends to come back to its expanded state. The gripping part 18 therefore forms rotationally activable first actuation means for deactivating said first retaining means (9, 19). Because of the longitudinal legs 20 being engaged in the cams 14, the pusher 7 moves distally and axially and does not rotate with respect to the distal part 17 of the holder body 15 hold by the user.

The distal movement of the pusher 7 causes the piston rod 13 to move distally and to push the piston 4 towards the distal end 2b of the container 2, thereby causing at least a part of the product 3 to be expelled via the nozzle 5.

The distal movement of the pusher 7 continues until it is stopped by the stop 19 coming in abutment with the distal faces 11a of the second projecting shapes 11, as shown on FIGS. 3, 4 and 9. In this first position, the first predetermined dose of the product 3 has been expelled, as shown on FIG. 9. The spring 22 therefore forms first biasing means for urging the pusher in the distal direction, from its initial position to its first position. Moreover, in this first position of the pusher 7, the spring 22 is still in a partially compressed state. As clearly appears from FIGS. 3 and 4, the distal face of the second projecting shape 11 and the proximal face of the stop 19 form respectively a second relief surface 11a and a second complementary surface 19a which are engaged in one another, thereby constituting second retaining means for maintaining said pusher 7 in said first position. Said second relief surface 11a and said second complementary surface 19a have, in this example, triangular complementary shapes.

In the embodiment shown on these figures, the rotation of the first actuation means, namely the gripping part 18 of the proximal part 16, has caused the deactivation of the first retaining means (9, 19).

It must be noted that in the example shown on FIG. 3, the user has rotated the proximal part 16 to the right of the figure: thanks to the fact that each first relief surface 9a is provided with two second complementary surfaces 11a located on either side of said first relief surface 9a, the user could have indifferently rotated the proximal part 16 to the left of the figure to attain the same result, namely the delivery of the first predetermined dose of the product 3. In another embodiment not shown, each first relief surface is provided with a single second complementary surfaces located either on one side or the other of said first relief surface, for example to be adapted to right or left hand writing users.

In order to proceed with the delivery of the second predetermined dose of the product 3, the user causes a second rotation of the proximal part 16 with respect to the distal part 17, by acting on the gripping part 18. On the example shown, this second rotation is completed in the same direction, namely to the right of the FIG. 3, than the first rotation described above.

By rotating the proximal part 16 a second time, the user causes the second relief surface 11a to disengage from the second complementary relief surface 19a, freeing the pusher 7, which is pushed distally under the force of the spring 22 which tends to come back to its expanded state. The gripping part 18 therefore forms rotationally activable second actuation means for deactivating said second retaining means (11, 19). Because of the longitudinal legs 20 being engaged in the cams 14, the pusher 7 moves distally and axially and does not rotate with respect to the distal part 17 of the holder body 15 hold by the user.

The longitudinal legs 20 and the cams 14 therefore form guiding means for preventing said pusher 7 to rotate with respect to said distal part 17 when said proximal part 16 is rotated by the user and that said pusher 7 moves from its initial position to its first position, and then from its first position to its second position.

The distal movement of the pusher 7 causes the piston rod 13 to move distally and to push the piston 4 towards the distal end 2b of the container 2, thereby causing the second dose of the product 3 to be expelled via the nozzle 5, as shown on FIG. 10. The shown device 1 is dimensioned such that, when the second dose of product 3 is expelled, there is no more product 3 left in the container, the product 3 has been used in an optimal way with no waste.

The distal movement of the pusher 7 continues until it is stopped by the spring 22 reaching its rest state, as shown on FIGS. 5, 6 and 10. In this second position of the pusher 7, the second predetermined dose of the product 3 has been expelled, as shown on FIG. 10. The spring 22 therefore forms second biasing means for urging the pusher in the distal direction, from its first position to its second position. The device 1 may comprise third retaining means (not shown) for maintaining the pusher 7 in this second position.

In the embodiment shown on these figures, the rotation of the second actuation means, namely the gripping part 18 of the proximal part 16, has caused the deactivation of the second retaining means (11, 19).

In the embodiment shown on these figures, the first actuation means and the second actuation means are therefore confounded and take the form of the gripping part 18 of the proximal part 16 or of the proximal part 16 itself. In this example also, the first and second biasing means are confounded and are under the form of one single helical spring 22.

In another embodiment of the invention not shown, the first projecting shapes 9 are not connected to the second projecting shapes 11 by a longitudinal projecting ridge 10 and the second predetermined dose of the product 3 can be delivered when the user causes a second rotation of the proximal part 16 with respect to the distal part 17 in the opposite direction than the first rotation he applied to deliver the first dose.

In another embodiment of the invention not shown, the device further comprises third projecting shapes, proximally spaced from said second projecting shapes and laterally located on one side, or on each side of said second projecting shapes, these third projecting shapes defining with the second complementary surface, third retaining means. When said proximal part is rotated by the user, said pusher moves from its second position to a third position in which a third dose of product has been expelled. Similarly, the device, according to the invention, may comprise additional projecting shapes defining additional positions to the pusher, allowing to successively expel additional doses of the product.

In reference to FIGS. 15 to 29 is described a second embodiment of the device of the invention, comprising automatic rotating means for causing the rotation of the pusher with respect to the holder body. In the embodiment of FIGS. 15-29, the first and second actuation means are rotationally and additionally axially displaceable, the combination of the rotational displacement and of the axial displacement of said first and second actuation means causing the deactivation of the first and second retaining means.

On FIG. 15 is represented a device 101, for the delivery of at least two predetermined doses of a product 3 comprising a container 2 defining a reservoir for containing the product 3 to be delivered. Like in the previous embodiment, the container 2 has an open proximal end 2*a* and a distal end 2*b* defining an outlet port in combination with said reservoir 2 and through which the product 3 is intended to be expelled. The distal end 2*b* of the container 2 is provided with a nozzle 5 (visible on FIGS. 17-22) through which the product 3 is intended to be expelled under the form of droplets. On FIGS. 15 and 16, said nozzle 5 is covered by a protection cap 6 in order to keep it clean and avoid any leakage of the product 3 in the storage position.

The device 101 of FIG. 15 further comprises a piston 4 movable with respect to said reservoir and a pusher 107. As will appear later, the pusher 107 is movable with respect to the container 2 for causing the piston 4 to move in the distal direction successively from an initial position, in which none of the product 3 has been expelled, to a first position, in which a first predetermined dose of the product 3 has been expelled, and to a second position, in which a second dose of the product 3 has been expelled.

The device 101 of FIG. 15 also comprises a holder body 120 receiving said container 2 and said pusher 107. On the example shown, this holder body 120 is made of two parts, a proximal part 121 and a distal part 122. The proximal part 121 and the distal part 122 are connected to each other by snap fitting. In an embodiment of the invention not shown, the two parts (121, 122) could be connected to each other either by gluing, screwing or by any classical means for connecting two parts together.

The device 101 of FIGS. 15 and 16 further comprises a button 133 located between the holder body 120 and the pusher 107, and a helical spring 132 located between the pusher 107 and the button 133. In another embodiment not shown, the helical spring can be located between the pusher and the holder body.

In reference with FIGS. 23 and 24, the pusher 107 has the global shape of a cylinder 108 having a substantially closed proximal end 108*a* and an open distal end 108*b*. The cylinder 108 is provided on its outer wall with projecting shapes (109, 110, 111, 112) protruding outwardly. In particular, the cylinder 108 is provided in its distal region with two first projecting shapes 109, diametrically opposed, among which only one is visible on FIG. 23. Each of these two first projecting shapes 109 is adjacent to one second projecting shape 110, proximally spaced from said first projecting shape 109. Each first projecting shape 109 is linked to the distal end 108*b* of the cylinder 108 by a first longitudinal projecting ridge 111. Moreover each first projecting shape 109 is linked to its adjacent second projecting shape 110 by a second longitudinal projecting ridge 112.

The respective distal faces of these first and second projecting shapes (109, 110) form relief surfaces (109*a*, 110*a*), the function of which will be explained later.

The second projecting shapes 110 extend proximally to reach the proximal end 108*a* of said cylinder 108 along a lateral face 114.

Extending from the inner face of the substantially closed proximal end 108*a* of the cylinder 108 (see FIG. 15) is a piston rod 113, the distal end 113*a* of which protrudes outside said cylinder 108, as shown on FIG. 23. The distal end 113*a* of said piston rod 113 is intended to be coupled with the piston 4, as shown on FIG. 15.

As can be seen from FIG. 24, the proximal end 108*a* of the cylinder 108 is substantially closed by a transversal wall 116 in which are cut two flexible tongues 117 which are able to be deflected in the plane of said transversal wall 116. Each tongue 117 has a foot 117*a*, by which it is fixed to the proximal end 108*a* of said cylinder 108, and a free end 117*b*. The transversal wall 116 is also provided on its outer face with radial stops 117*c* and projections 115 extending in the proximal direction.

The cylinder 108 is also provided on its outer lateral wall with two third projecting shapes, diametrically opposed, having lateral faces 118 and proximal faces 119.

In reference to FIG. 27, is shown the distal part 122 of the holder body 120. As appears clearly on this figure, the inner wall of the distal part 122 is provided with two diametrically opposed first inclined shapes 127 (only one being visible on FIG. 27) projecting inwardly. Each first inclined shape 127 is adjacent to a radial stop 128. The proximal face 128*a* of said radial stop 128 forms a relief surface, the function of which will be explained later. The outer wall of the distal part 122 is provided at its proximal end with two diametrically opposed proximally projecting shapes 129, only one being visible on FIG. 27. The distal part 122 is also provided on its outer wall with two diametrically opposed wings 130 for the gripping of the holder body 120.

Within the distal part 122 is present an internal skirt 131 forming an opening for the nozzle 5 to pass through at the distal end of said distal part 122.

In reference with FIG. 28 is shown the proximal part 121 of the holder body 120. The outer wall of the proximal part 121 is provided at its distal end with two diametrically opposed recesses 124. These recesses are intended to engage with the proximally projecting shapes 129 of the distal part 122, in order to connect the proximal part 121 to the distal part 122 and block the rotation of said proximal part 121 with respect to said distal part 122.

The proximal part 121 is further provided on its inner wall with two diametrically opposed second inclined shapes 123, projecting inwardly, only one being visible on FIG. 28. In the distal region of the proximal part 121, the inner wall is provided with an annular ridge 125. The bottom of the proximal part 121 is provided with an opening 126. As will appear from the description of FIG. 29, this opening 126 is for the proximal part of the button 133 to be able to protrude outside said holder body 120.

In reference with FIG. 29, there is shown the button 133. The button 133 has the global shape of a cylinder substantially closed at its proximal end and open at its distal end. The proximal end of the button 133 is provided with a proximal pressing surface 134, protruding proximally through the opening 126 and intended to be pressed by the user in order to start the delivery of the successive doses of the product 3. The cylindrical wall 139 of the button 133 is provided with various cuts: in the proximal region of the wall 139, said wall 139 is provided with two diametrically opposed cuts (only one being visible on FIG. 29), each cut defining a first slope 136. The wall 139 is further provided, in its distal region, with two diametrically opposed second cuts, each defining a second slope 135. Each second slope 135 is adjacent to a third slope 137.

The inner wall of the button 133 is provided with two diametrically opposed longitudinal ridges 138, only one being visible on FIG. 29.

The operation of the device 101 will now be described in reference to FIGS. 15-22, 26 and 27.

The device 101 is provided to the user before use in the storage position shown on FIGS. 15 and 16. In this position, the nozzle 5 is protected with the cap 6. Once the cap 6 is removed, the device 101 is in the initial position. The initial position corresponds to the FIGS. 15 and 16 once the cap 6 has been removed.

In this initial position, the spring 132 is at least partially compressed. The distal end of said spring 132 is bearing on the proximal end 108a of the cylinder 108 forming the pusher 107 and the proximal end of said spring 132 is bearing on the inner face of the button 133. In this position, the pusher 107 is received within the button 133 and the button 133 is received within the proximal part 121 of the holder body 120.

In the initial position, the longitudinal ridges 138 are in abutment against the lateral faces 118 of the cylinder 108 on the pusher 107, thereby coupling the button 133 to the pusher 107 in the counter clockwise rotation direction. As shown on FIG. 25, in this initial position, the clockwise rotation of the pusher 107 with respect to the button 133 is not impeded.

In this position, the proximal pressing surface 134 of the button 133 protrudes from the proximal part 121 of the holder body 120 by passing through the opening 126 of the proximal part 121.

In this initial position, as shown on FIG. 16, the first inclined shapes 127 are in abutment on the second slopes 135 but they are not engaged in each other. Moreover, the second inclined shapes 123 are in abutment on the first slopes 136.

As will appear later, the first and second slopes form a set of first ramps (135, 136) intended to cooperate with a set of second ramps (123, 127) formed by the first and second inclined shapes so as to cause the rotation of said button 133 with respect to said holder body 120 when a distal force is exerted on, or released from, said proximal pressing surface 134 of said button 133. These two sets of ramps (123, 127, 135, 136) are part of automatic rotating means for causing the rotation of said pusher 107 with respect to said holder body 120 when first and/or second actuation means such as the proximal pressing surface 134 of the button 133 are axially activated.

As appears clearly on FIG. 16, the distal face of the first projecting shape 109 and the proximal face of the radial stop 128 form respectively a first relief surface 109a and a first complementary relief surface 128a which are engaged in each other thereby constituting first retaining means of the pusher 107 in the initial position.

In this initial position, the piston 4 has not moved from its position before use shown on FIG. 15 and none of the product 3 has been expelled yet.

In order to proceed with the delivery of the first predetermined dose of the product 3, the user seizes the device 101, for example with one hand, and he presses distally and axially on the proximal pressing surface 134 of the button 133.

The distal pressure exerted by the user on the proximal pressing surface 134 of the button 133 forces the second slopes 135, which are in abutment against the first inclined shapes 127, to slide along said first inclined shapes 127, thereby causing both the rotation and the distal translation of the button 133, with respect to the holder body 120, as shown on FIG. 18. At the same time, the first slopes 136 slide along the second inclined shapes 123.

The pusher 107 being coupled to the button 133 in counter clockwise rotation thanks to the longitudinal ridges 138 being in abutment against the radial stop 117c, the pusher 107 also rotates with respect to the holder body 120, and in particular with respect with the distal part 122 of said holder body 120, thereby disengaging the first relief surface 109a from the first complementary surface 128a.

Before the disengagement of the first relief surface 109a from the first complementary surface 128a is effective, the piston 4 has not moved as shown on FIG. 17.

Once the first relief surface 109a and the first complementary surface 128a are disengaged from each other, the spring 132 is freed and tends to come back to its expanded state, thereby pushing the pusher 107 in the distal direction.

In the embodiment shown on this figures, the rotation of the first actuation means, namely the button 133, has caused part of the deactivation of the first retaining means (109, 128). Moreover, the combination of the rotation displacement and of the additional axial displacement of the button 133 has caused the deactivation of the first retaining means.

The button 133 therefore forms a rotationally and axially activable first actuation means for deactivating the first retaining means (109, 128).

The distal movement of the pusher 107 causes the piston rod 113 to move distally and to push the piston 4 towards the distal end 2b of the container 2, thereby causing at least a part of the product 3 to be expelled via the nozzle 5, as shown on FIG. 19.

The distal movement of the pusher 107 continues until it is stopped by the second projecting shape 110 coming in abutment with the radial stop 128, as shown on FIG. 20. In this first position of the pusher 107, the first predetermined dose of the product 3 has been expelled, as shown on FIG. 19. The spring 132 therefore forms first biasing means for urging the pusher 107 in the distal direction, from its initial position to its first position. Moreover, the spring 132 is still in a partially compressed state. As clearly appears from FIG. 20, the distal face of the second projecting shape 110 and the proximal face of the radial stop 128 form respectively a second relief surface 110a and a second complementary surface 128a which are engaged in one another, thereby constituting second retaining means for maintaining said pusher 107 in said first position.

The user then releases the distal pressure he exerted on the proximal part 134 of the button 133. Thanks to the spring 132 tending to come back to its expanded state, the button 133 is pushed back in the proximal direction. The first slopes 136, in abutment against the second inclined shapes 123, slide along said second inclined shapes 123. At the same time, the second slopes 135 slides along the first inclined shapes 127. In consequence, the button 133, while moving back in the proximal direction, also rotates back, and comes back in its initial position, as shown on FIG. 20. During the return of the button 133 to its initial position, the pusher 107 has been maintained in an immobile state with respect to the holder body 120, thanks to the spring 132 pushing said second projection shape 110 and the second longitudinal ridge 112 against said radial stop 128.

In consequence, as shown on FIG. 25, since the clockwise rotation of the pusher 107 with respect to the button 133 is not impeded, the pusher 107 rotates clockwise with respect to the button 133 and the elastically deformable free end 117b of the flexible tongue 117 is deflected and slides along the inner wall of the button 133, passes over the annular ridge 138 and returns to its rest state while the free end 117b comes in abutment with said annular ridge 138, as shown on FIG. 26. In this position then, the pusher 107 is again coupled to the button 133 in the counter clockwise rotation direction.

In this embodiment of the invention, the radial stop 117c and the free end 117b therefore form respectively one first rotation stop and one second rotation stop cooperating with one rotation abutment formed by the annular ridge 138, so as to cause the rotation of said pusher 107 or button 133 with respect to said holder body 120, when said button 133 rotates when a distal force is exerted on said proximal pressing surface 134 of said button 133.

In order to proceed with the delivery of the second predetermined dose of the product 3, the user then repeats the same operation as for the first dose: he presses on the proximal part 134 of the button 133, the first slopes 136 cooperate with the second inclined shapes 123, the second slopes 135 cooperate with the first inclined shapes 127 so as to cause the rotation and distal translation of both the button 133 and the pusher 107, thereby disengaging the second relief surface 110a from the second complementary surface 128a. The spring 132 is therefore freed and tends to come back in its expanded position, thereby pushing the pusher 107 in the distal direction.

In the embodiment shown on this figures, the rotation of the second actuation means, namely the button 133, has caused part of the deactivation of the second retaining means (109, 128). Moreover, the combination of the rotation displacement and of the additional axial displacement of the button 133 has caused the deactivation of the second retaining means.

The button 133 therefore forms a rotationally and axially activable second actuation means for deactivating the second retaining means (110, 128).

The distal movement of the pusher 107 causes the piston rod 113 to move distally and to push the piston 4 towards the distal end of the container 2, thereby causing the second dose of the product 3 to be expelled via the nozzle 5, as shown on FIG. 21.

The distal movement of the pusher 107 continues until it is stopped by the spring 132 reaching its expanded state, as shown on FIG. 22. The pusher 107 is then in its second position. The spring 132 therefore forms second biasing means for urging the pusher 107 in the distal direction, from its first position to its second position.

In the embodiment shown on these figures, the first actuation means and the second actuation means are therefore confounded and take the form of the button 133. In this example also, the first and second biasing means are confounded and are under the form of one single helical spring 132.

In an embodiment of the invention not shown, the device further comprises third retaining means for maintaining the pusher 107 in the second position.

In another embodiment of the invention not shown, the device further comprises second flexible tongues and third projecting shapes allowing the successive delivery of a third dose of the product.

The devices of the invention is an improvement over the nasal and/or oral spray and/or injection devices of the prior art. Thanks to the device of the invention, it is possible to deliver successively two or more doses of product in a very reproducible way. Moreover, it is possible to complete such an operation with only one hand.

The invention claimed is:

1. Device (1; 101) for the successive delivery of at least two predetermined doses of a product (3), comprising:
 a container (2) defining a reservoir for containing the product (3) to be delivered, said container (2) having an open proximal end (2a), and a distal end (2b) defining an outlet port in combination with said reservoir and through which the product (3) may be delivered,
 a piston (4) movable with respect to said reservoir, the distal movement of said piston (4) causing at least part of the product (3) to be expelled from said container (2),
 a pusher (7; 107) movable with respect to said container (2) for causing said piston (4) to move in the distal direction successively from an initial position, in which none of said product (3) has been expelled to a first position, in which a first dose of said product (3) has been expelled, and to a second position, in which a second dose of said product (3) has been expelled,
 a holder body (15; 120), intended to receive at least part of said container (2) and said pusher (7; 107),
 first biasing means (22; 132) designed for tending to urge said pusher (7; 107) in the distal direction, at least from the initial position to the first position,
 first retaining means (9, 19; 109, 128) designed for maintaining said pusher (7, 107) in said initial position,
 first actuation means (18; 133, 134) designed for deactivating said first retaining means (9, 19; 109, 128) and allowing the distal displacement of said pusher (7; 107) at least from the initial to the first positions,
 second biasing means (22; 132) designed for tending to urge said pusher (7; 107) in the distal direction from the first position to at least said second position,
 second retaining means (11, 19; 110, 128) designed for maintaining said pusher (7, 107) in said first position,
 second actuation means (18; 133, 134) designed for deactivating said second retaining means (11, 19; 110, 128) and allowing the distal displacement of said pusher (7; 107) at least from the first to the second positions,
 characterized in that
 said first and second actuation means (18; 133, 134) are rotationally displaceable to cause the deactivation of said first and second retaining means (9, 11, 19: 109, 110 128), respectively.

2. Device (1; 101) according to claim 1, characterized in that said first and/or second actuation means (133, 134) are additionally at least axially displaceable, the combination of said rotation and said axial displacement causing the deactivation of said first and/or second retaining means (9, 11, 19: 109, 110 128).

3. Device (1; 101) according to claim 1, characterized in that said first and second actuation means (18; 133, 134) are confounded.

4. Device (1; 101) according to claim 1, characterized in that said first and second biasing means (22; 132) are confounded.

5. Device (1; 101) according to claim 1, characterized in that said pusher (7, 107) being able to rotate with respect to at least part (16; 121, 122) of said holder body (15; 120), said first retaining means (9, 19; 109, 128) are deactivated by a first rotation of said pusher (7, 107) with respect to said part (16; 121, 122) of said holder body (15; 120).

6. Device (1; 101) according to claim 5, characterized in that said second retaining means (11, 19; 110, 128) are deactivated by a second rotation of said pusher (7, 107) with respect to said part (16; 121, 122) of said holder body (15; 120).

7. Device (1; 101) according to claim 5, characterized in that said first retaining means (9, 19; 109, 128) comprise at least a first relief surface (9a; 109a) formed on the outer wall of said pusher (7, 107) and at least a first complementary relief surface (19a; 128a) formed on the inner wall of said part (16; 122) of said holder body (15; 120), said first and first complementary relief surfaces (9a, 19a; 109a, 128a) cooperating so as to be engaged in one another in the initial position and disengaged from one another after said first rotation of said pusher (7, 107) with respect to said part (16; 122) of said holder body (15; 120).

8. Device (1; 101) according to claim 6, characterized in that said second retaining means (11, 19; 110, 128) comprise at least a second relief surface (11a; 110a) formed on the outer wall of said pusher (7, 107) and at least a second complementary relief surface (19a; 128a) formed on the inner wall of said part (16; 122) of said holder body (15; 120), said second relief surface and second complementary relief surface (11a, 19a, 110a, 128a) cooperating so as to be engaged in one another in the first position and disengaged from one another after said second rotation of said pusher (7, 107) with respect to said part (16; 122) of said holder body (15; 120).

9. Device (1; 101) according to claim 7, characterized in that said first relief surface (9a; 109a) and/or said first complementary relief surface (19a; 128a) are chosen in the group comprising a radial stop, a radially projecting surface, a cam, a recess.

10. Device (1) according to claim 1, characterized in that said holder body (15) comprises at least two parts, a proximal part (16) and a distal part (17) which are able to rotate one with respect to the other, said distal part (17) being coupled to said container (2), said pusher (7) being able to rotate with respect to said proximal part (16), said proximal part (16) forming at least in part said rotationally activable first and/or second actuation means (18), said device (1) comprising guiding means (14, 20) for preventing said pusher (7) to rotate with respect to said distal part (17) when said proximal part (16) is rotated by the user and that said pusher (7) moves from its initial position to its first position, and then from its first position to its second position.

11. Device (1) according to claim 10, characterized in that said guiding means (14, 20) are partly formed on said pusher (7) and partly formed on said distal part (17) of said holder body (15).

12. Device (1) according to claim 11, characterized in that said guiding means comprises at least a longitudinal cam (14) formed on the pusher (7) and at least a longitudinal leg (20) formed on said distal part (17) of said holder body (15), said longitudinal leg (20) being engaged into said longitudinal cam (14) at least from the initial position to said second position of said pusher (7).

13. Device (1) according to claim 7, characterized in that it comprises two second complementary relief surfaces (11a), one being laterally located on one side of said first relief surface (9, 9a) and the other one being laterally located on the other side of said first relief surface (9, 9a).

14. Device according to claim 7, characterized in that it comprises two second relief surfaces, one being laterally located on one side of said first relief surface and the other one being laterally located on the other side of said first relief surface.

15. Device (1) according to claim 7, characterized in that said first relief surface (9a; 109a) and first complementary relief surface (19a; 128a) have triangular respectively complementary shapes.

16. Device (101) according to claim 2, characterized in that it further comprises automatic rotating means (117a, 117b, 138, 123, 127, 135, 136) for causing the rotation of said pusher (107) with respect to said holder body (120) when said first and/or second actuation means (133, 134) are axially activated.

17. Device (101) according to claim 16, characterized in that said first and/or second actuation means comprise at least one button (133), said button (133) being received in said holder body (120), said button (133) being movable in translation and in rotation within said holder body (120), said button (133) comprising a proximal pressing surface (134), said proximal pressing surface (134) extending outwardly and proximally from said holder body (120).

18. Device (101) according to claim 17, characterized in that said automatic rotating means (117a, 117b, 138, 123, 127, 135, 136) comprise at least one first ramp (135, 136) provided on said button (133) and at least one second ramp (123, 127) provided on said holder body (120), said first and second ramps (123, 127, 135, 136) cooperating with each other so as to cause the rotation of said button (133) with respect to said holder body (120), when a distal force is exerted on, or released from, said proximal pressing surface (134) of said button (133).

19. Device (101) according to claim 17, characterized in that said automatic rotating means (117a, 117b, 138, 123, 127, 135, 136) comprise at least one first rotation stop (117a) and one second rotation stop (117c) provided on said pusher (107) or on said button (133) and one rotation abutment (138) respectively located on said button (133) or on said pusher (107), said first and second rotation stops (117a), 117c) and said rotation abutment (138) successively cooperating with each other so as to cause the rotation of said pusher (107) or button (133) with respect to said holder body (120), when said button (133) rotates when a distal force is exerted on its said proximal pressing surface (134).

20. Device (101) according to claim 19, characterized in that said second rotation stop (117b) is elastically deformable to pass over said rotation abutment (138) after said first position is reached by said pusher (107) and to abut against said rotation abutment (138) between first and second positions.

21. Device (1; 101) according to claim 1, characterized in that said first and/or second biasing means comprise at least one helical spring (22; 132).

22. Device (1; 101) according to claim 1, characterized in that it further comprises third retaining means for maintaining said pusher (7; 107) in said second position.

23. Device (1; 101) according to claim 8, characterized in that said second relief surface (11a; 110a) and/or said second complementary relief surface (19a; 128a) are chosen in the group comprising a radial stop, a radially projecting surface, a cam, a recess.

24. Device (1) according to claim 8, characterized in that said second relief surface (11a; 110a) and second complementary relief surface (19a; 128a) have triangular respectively complementary shapes.

* * * * *

UNITED STATES PATENT AND TRADEMARK OFFICE
CERTIFICATE OF CORRECTION

PATENT NO.       : 8,568,358 B2  
APPLICATION NO.  : 12/514625  
DATED            : October 29, 2013  
INVENTOR(S)      : Grunhut et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1135 days.

Signed and Sealed this

Fifteenth Day of September, 2015

Michelle K. Lee
*Director of the United States Patent and Trademark Office*